United States Patent
Messinger

(10) Patent No.: US 10,265,700 B2
(45) Date of Patent: Apr. 23, 2019

(54) SYSTEM FOR IMPROVING DIABETES TESTING AND REDUCING COUNTERFEITING

(71) Applicant: Samuel Messinger, Ramot Bet Shemish (IL)

(72) Inventor: Samuel Messinger, Ramot Bet Shemish (IL)

(*) Notice: Subject to any disclaimer, the term of this patent is extended or adjusted under 35 U.S.C. 154(b) by 0 days.

(21) Appl. No.: 15/422,236

(22) Filed: Feb. 1, 2017

(65) Prior Publication Data
US 2018/0135098 A1 May 17, 2018

Related U.S. Application Data

(60) Provisional application No. 62/421,105, filed on Nov. 11, 2016.

(51) Int. Cl.
| | |
|---|---|
| *B01L 3/00* | (2006.01) |
| *A61B 5/00* | (2006.01) |
| *G01N 35/00* | (2006.01) |

(52) U.S. Cl.
CPC ............ *B01L 3/52* (2013.01); *A61B 5/0002* (2013.01); *B01L 3/54* (2013.01); *G01N 35/00* (2013.01); *B01L 2200/141* (2013.01); *G01N 2035/00108* (2013.01)

(58) Field of Classification Search
None
See application file for complete search history.

(56) References Cited

U.S. PATENT DOCUMENTS

| | | | | |
|---|---|---|---|---|
| 4,476,149 A | * | 10/1984 | Poppe | G01N 33/521 101/223 |
| 5,251,758 A | * | 10/1993 | Kolacek | A47G 21/00 206/459.5 |
| 2003/0176183 A1 | * | 9/2003 | Drucker | A61B 5/743 455/414.1 |
| 2007/0053406 A1 | * | 3/2007 | LaGuardia | G01K 1/14 374/161 |
| 2007/0264165 A1 | * | 11/2007 | Chan | B65D 83/0829 422/400 |
| 2012/0203465 A1 | | 8/2012 | Callewaert et al. | |
| 2014/0131450 A1 | * | 5/2014 | Gordon | G06K 19/07749 235/492 |

FOREIGN PATENT DOCUMENTS

| | | |
|---|---|---|
| CN | 103228305 A | 7/2013 |
| WO | WO-2005/040793 A1 | 5/2005 |
| WO | WO-2009/053437 A1 | 4/2009 |

\* cited by examiner

Primary Examiner — Neil N Turk
(74) Attorney, Agent, or Firm — Carrie Stroup

(57) ABSTRACT

A diabetes test system for measuring blood glucose levels is provided, which includes a glucose meter, at least one diabetic test strip, and a container or pouch for storing the diabetes test strips and protecting them during transport. Methods of packaging diabetes test strips are also provided. The glucose meter includes software for detecting the validity of the at least one diabetic test strip, and a communication device that transmits data relating to the blood glucose level of the user to an external device. A secure packaging system for diabetes test strips which eliminates gray market sales of such test strips is also provided.

10 Claims, 22 Drawing Sheets

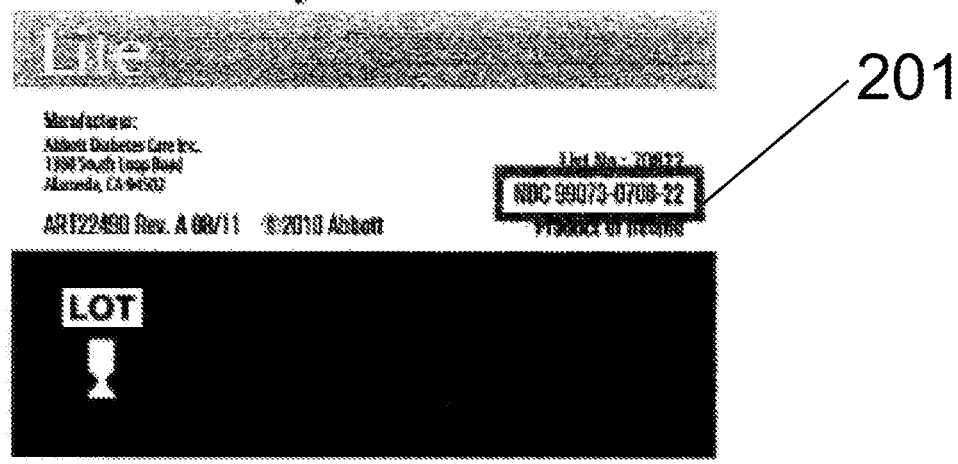
Bottom image of U.S. retail box of FreeStyle Lite test strips
FIG. 18

Front image of U.S. retail box of FreeStyle Lite test strips
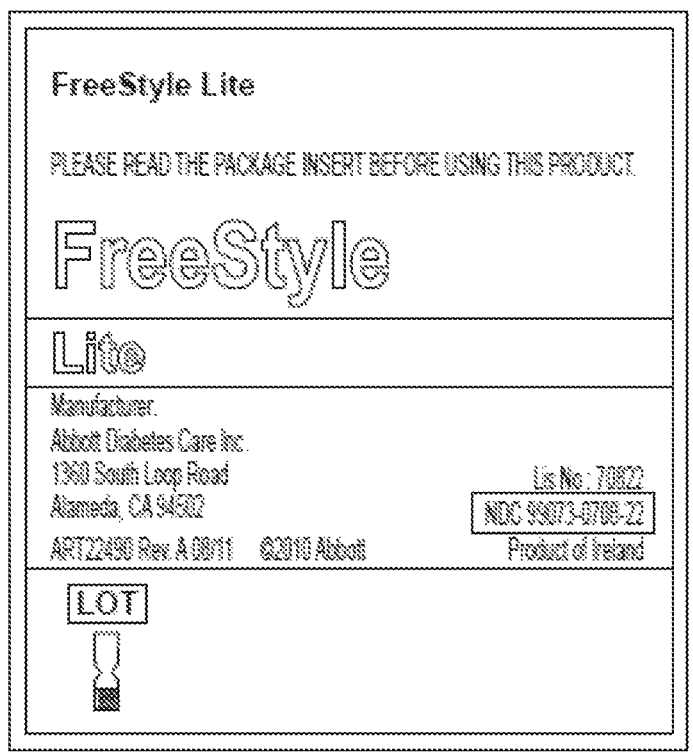
Bottom image of U.S. retail box of FreeStyle Lite test strips
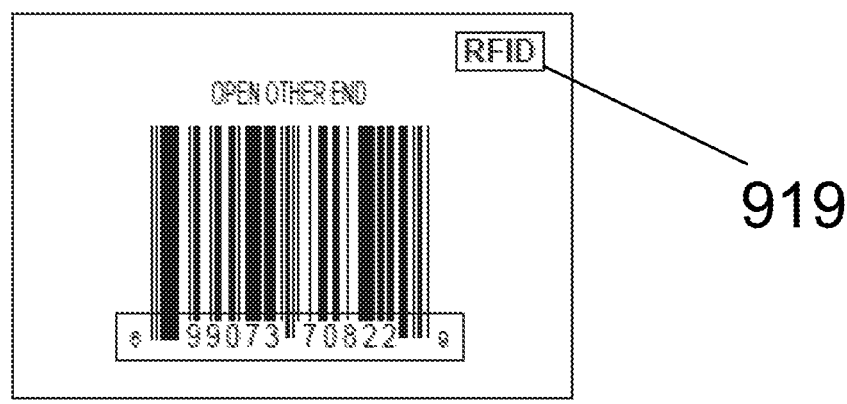
919
FreeStyle test strips that are intended for sale outside the United States do not have an NDC number. Id. ¶ 6-7.
FIG. 19

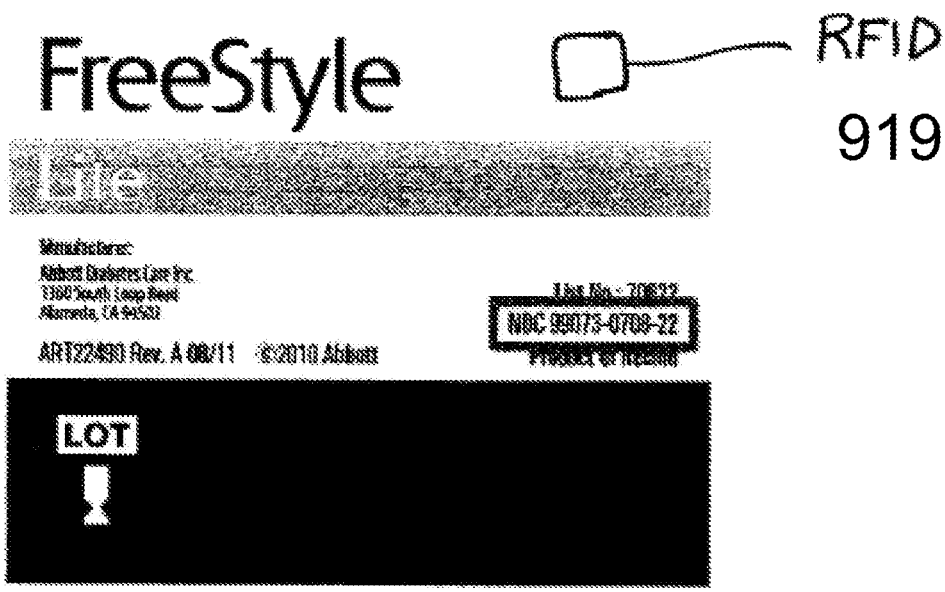
Bottom image of U.S. retail box of FreeStyle Lite test strips
FIG. 20 ately 0.3 microliters. An
SYSTEM FOR IMPROVING DIABETES TESTING AND REDUCING COUNTERFEITING

CROSS-REFERENCE TO RELATED APPLICATIONS

The present application claims priority to U.S. Provisional Patent Application No. 62/421,105 filed Nov. 11, 2016, which is incorporated by reference herein in its entirety.

FIELD OF THE INVENTION

The invention relates primarily to sealed diabetes test strips and diabetes test systems including the same. More specifically, the invention relates to sanitary test strips easily and economically dispensed from a container or diabetes pouch. The invention also provide systems and methods of validating the authenticity of diabetes test strips.

BACKGROUND OF THE INVENTION

Diabetes is a disease impairing a person's ability to produce or respond to insulin, thus elevating levels of glucose in the blood. Diabetes can cause long term and serious problems, including multiple organ failure, heart attack, blindness, amputation and nerve damage. One way diabetics monitor their blood glucose levels is by using diabetes test strips, which work by converting glucose in the blood into an electrical current. Each test strip has a unique formulation of enzymes that works as a catalyst. Present day test strips use various chemistries, such as GDH-PQQ with nPBI inhibitor mediator (Osmium complex with n-pentyl benzimidazole ligand) or GDH-FAD with MAP mediator n-methyl pyridine. Typically, a test sample of blood is obtained from the user, approximately 0.3 microliters. An electrical current is produced on test strip and travels on gold plated circuits to be converted into an electrochemical signal for the glucose meter to display. Details of the workings of a glucose meter may be found, for example, in Dr. Erika Gebel, *Electrochemical Test Strips*, DIABETES FORECAST, 2012.

Since diabetes is a long term disease spanning the lifetime of the diabetic, many test strips are used by the diabetic throughout his or her lifetime. For example, type 1 diabetics may take as many as 30 glucose readings daily. Test strips are expensive, usually costing $0.40 to $1.00 each, and in some cases as much as $2.00 each. As such, test strips which become unusable for a variety of reasons, as set forth below, can cost the diabetic a substantial amount of money. Moreover, diabetes test strips are susceptible to counterfeiting and inaccurate test readings. Inaccurate readings can have a substantial impact, including altering administered dosage levels, as well as medical implications such as, loss of eyesight, liver and kidney damage, and poor circulation. Poor circulation in diabetics has long resulted in loss of limbs, especially feet. Medical implications for incorrect dosages based on erroneous readings have even resulted in death in some cases.

Presently, test strips and particularly blood glucose test strips are sold loosely packed in plastic containers. Usually there are 50 strips in a container and the individual strips are difficult to access due to crowding. During the process of removing a single test strip for insertion in a separate glucose meter, the test strip may be compromised through contact with unsterile handling, such as with human fingers or by dropping it on the table or the ground from the container, thus resulting in contamination which can cause inaccurate or voided test readings.

Recalls also are a problem in the industry. In most cases, there are no issues with respect to manufacturing, but over time exposure to moisture and temperature variances and vibrational forces (see below) can lead to test strip degradation and failure. Historically, there have been recalls of test strips involving low readings that could cause a type 1 diabetic to over medicate, thus resulting in diabetic ketoacidosis.

For example, the transportation of test strips by land carrier, where there are road vibrations and exposure to G Forces from potholes and road bumps, as well as bearing and spring vibrations from vehicles and forklifts, may affect test strip enzyme performance due to the damage of the delicate enzymes present in the test strips. Interestingly, the fruit industry is acutely aware of this phenomenon and has underwritten many scientific tests to investigate cellular (enzyme) degradation from fruit transit. In one study, the placement in the truck of the boxes of fruit to be shipped was analyzed, and it was determined that boxes placed at lower levels experienced more degradation after shipment and careful testing. See Ran Zhou et al., *Effect of transport vibration levels on mechanical damage and physiological resposnes of Huanghua pears*, 46 POSTHARVEST BIOLOGY AND TECHNOLOGY 20-28 (2007). Tests on the degradation of enzymes of fruit during transport may also shed light on the effect of vibration on diabetes test strip failure.

Moisture is also a factor. The enzymes in the test strip are delicate and need to be hydrated and maintained in a specific moisture range for the test strip to perform properly or they will fail. Too much hydration will lead to degradation of the strip. Further, test strips are sensitive to temperature. Most test strips should be maintained at temperatures above at least 4 degrees C. and below 30 degrees C., and exposure to temperatures outside of this range can damage the enzymes.

Black and grey market test strips are also a major problem in the industry. Sales of black and grey market diabetes test strips result in significant lost revenue and profit. In the grey market, U.S.-based manufacturers of diabetes test strips ship these products outside of the United States for sale abroad. In some instances, these diabetes test strips are illegally imported back into the United States and sold to pharmacies for resale to the public. About 95% of all of these gray market sales are paid for by third-party insurance and the United States government, through Medicare or Medicaid, resulting in the loss of billions of dollars each year. Indeed, the quality of such grey market test strips and their handling are called into question and raise legal ramifications as well, where it is most likely that insurance companies, Medicare, or Medicaid paid for those test strips in the first place. On the other hand, in the black market, entirely counterfeit test strips are also a clear danger to a diabetic person, resulting in inaccurate readings, including low or high readings that cause an over or under medication, resulting in injury or even death.

Another issue with current diabetic test strip packaging is that present test strip containers are not ecologically viable. Test strips and test strip containers are used by the hundreds of millions each year and discarded into landfills. Most containers are made from plastic, which are often not recyclable and find their way to a waste dump.

Current packaging arrangements for test strips fail to meet patient needs for ensuring quality glucose readings. Several attempts have been made to solve some of the above-mentioned problems, such as those found in International Patent Application Publication No. WO 2009/053437 to Eisenhardt et al., U.S. Patent Application Publication No. 2012/0203465 to Callewaert et al., Chinese Patent Publication No. 103228305 to Day et al., and International Patent Application Publication No. WO 2005/040793 to Griffith et al. However, none of these attempts entirely solves the issue of quality degradation of test strips or gray market sales and counterfeiting.

As such, there exists a need for reliable device packaging for a glucose measurement system, including for diabetes test strips, that improves glucose level accuracy while reducing the potential for counterfeiting to protect the health of patients.

SUMMARY OF THE INVENTION

Accordingly, the invention provides a diabetes test system for measuring the blood glucose level of a user. One aspect of the invention provides improved test strip packaging that maintains the integrity of the diabetes test strips and conveys information on the range of temperatures and vibrational forces to which the test strips have been exposed to protect the diabetic user from relying on damaged strips. Another aspect of the invention provides a mechanism to ensure the authenticity of a diabetic test strip to reduce or eliminate the occurrence of grey and black market sales. Yet another aspect of the invention provides a diabetes test system which includes the diabetes test strips and packaging of the invention, and which further includes a glucose meter which is capable of transmitting data relating to the blood glucose level of the user to at least one external device.

In one embodiment, a diabetes test system is provided which includes a glucose meter, at least one diabetic test strip, and a container for storing the at least one diabetic test strip, the container formed of a body having a dispensing slot formed therein, and the dispensing slot being enclosed by a slot seal. The glucose meter includes a communication device that transmits data relating to the blood glucose level of the user to at least one external device.

The invention further provides a method for measuring blood sugar levels, the method including the steps of: inserting at least one diabetic test strip into a glucose meter, verifying a validity of the at least one diabetic test strip based on information displayed on the glucose meter, obtaining a blood sample from a user, contacting the blood sample to the at least one diabetic test strip, obtaining a blood glucose level from the glucose meter, and communicating data pertaining to the blood glucose level of the user to an external device.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 18 is an image of prior art labels for the front and bottom of a box of prior art diabetes test strips, including the bar code on the bottom of the box;

FIG. 19 is an image of labels for the front and bottom of a box of prior art diabetes test strips, including an RFID tag on the bottom of the box according to an embodiment of the invention;

FIG. 20 is an image of labels for the front and bottom of a box of prior art diabetes test strips, including an RFID tag on the front of the box according to an embodiment of the invention;

DETAILED DESCRIPTION

The invention provides a diabetes test system which includes significant improvements in diabetes test strip packaging and serves as a system and method for testing blood glucose level while ensuring the validity of the diabetic test strip. One aspect of the invention is directed to sealed and anti-counterfeit test strips that are easily and economically dispensed to the user. The invention also provides means for ensuring the validity of diabetes test strips from factory to end user. The invention also provides a means of communicating information from the diabetes test system to other devices or servers to assist the diabetic user.

Figure 1:
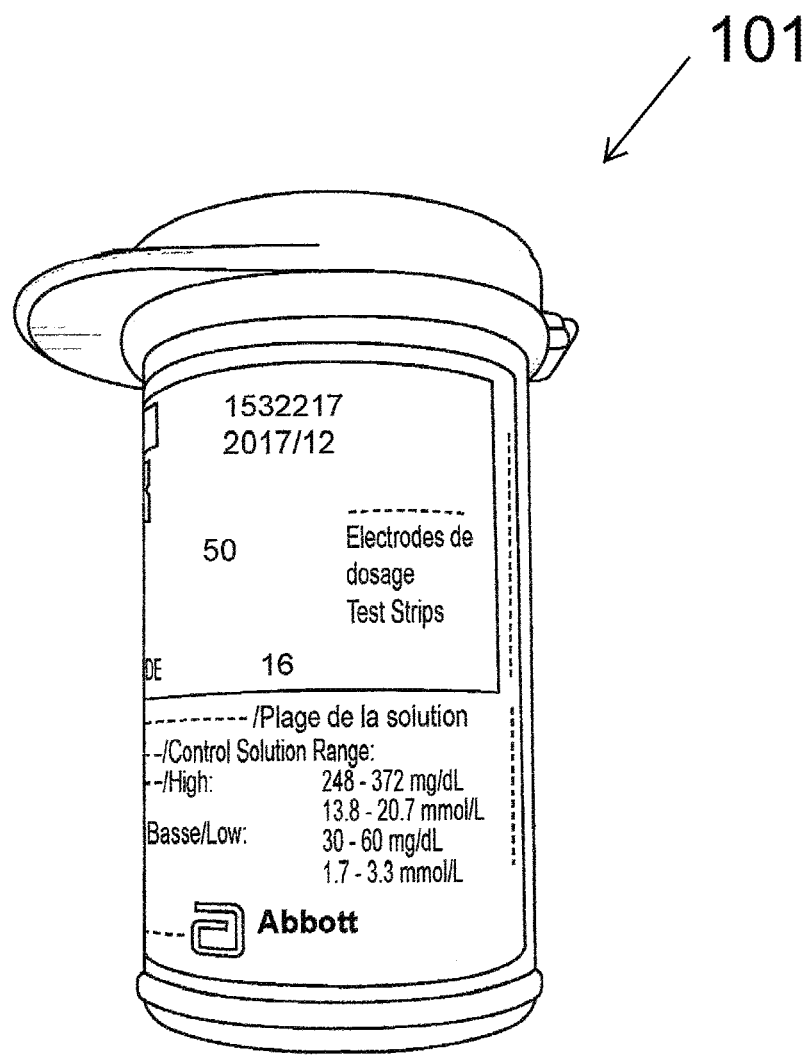
FIG. 1 is a front perspective view of a prior art container for diabetes test strips.
Figure 2:
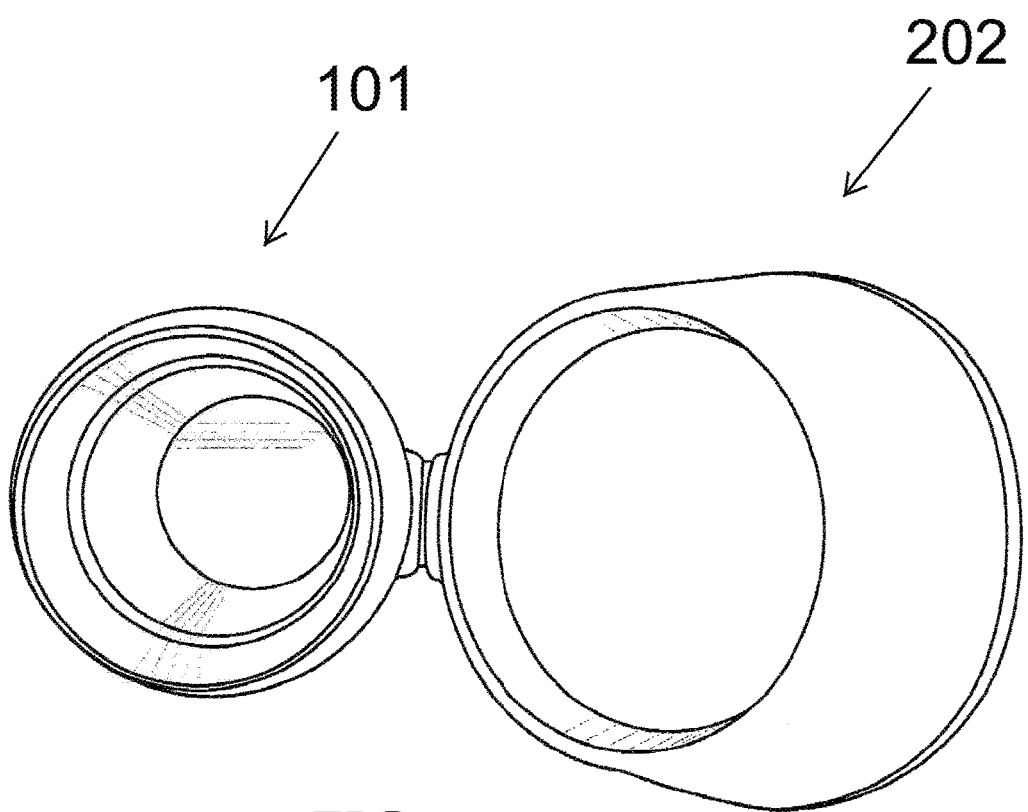
FIG. 2 is a top view of the container of FIG. 1 in an open position.
Figure 3:
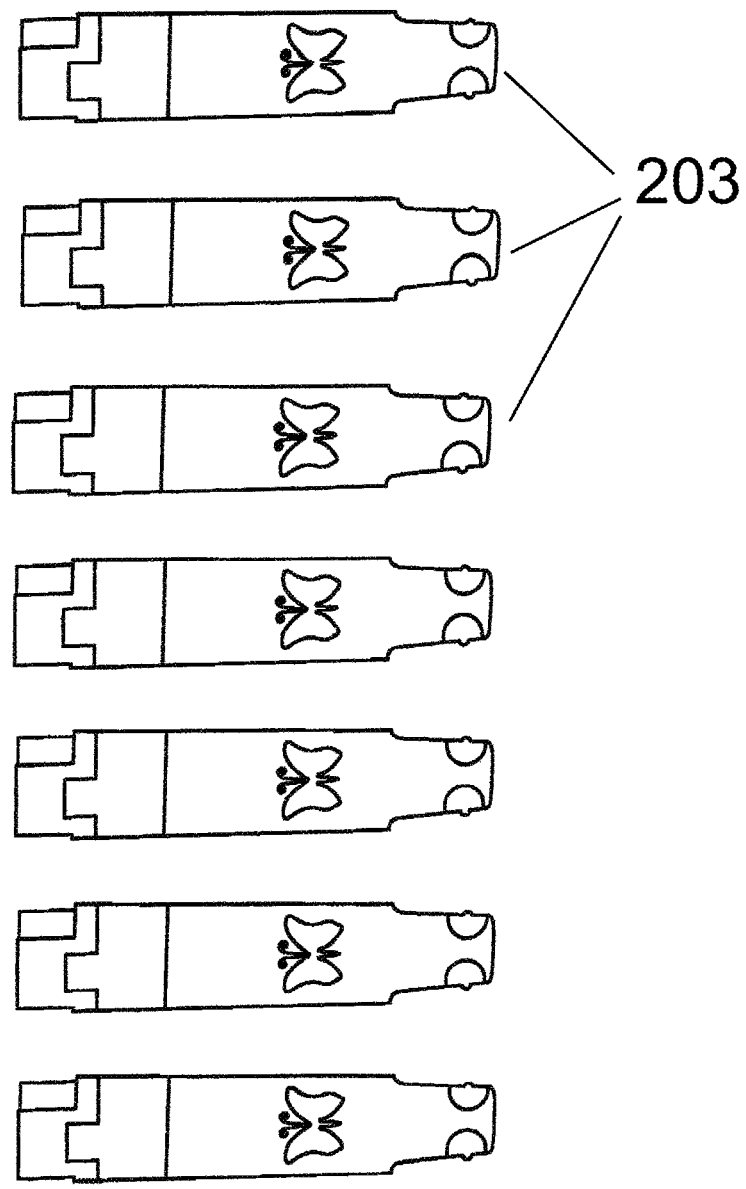
FIG. 3 is a top plan view of individual diabetes test strips known in the art.
Figure 4:
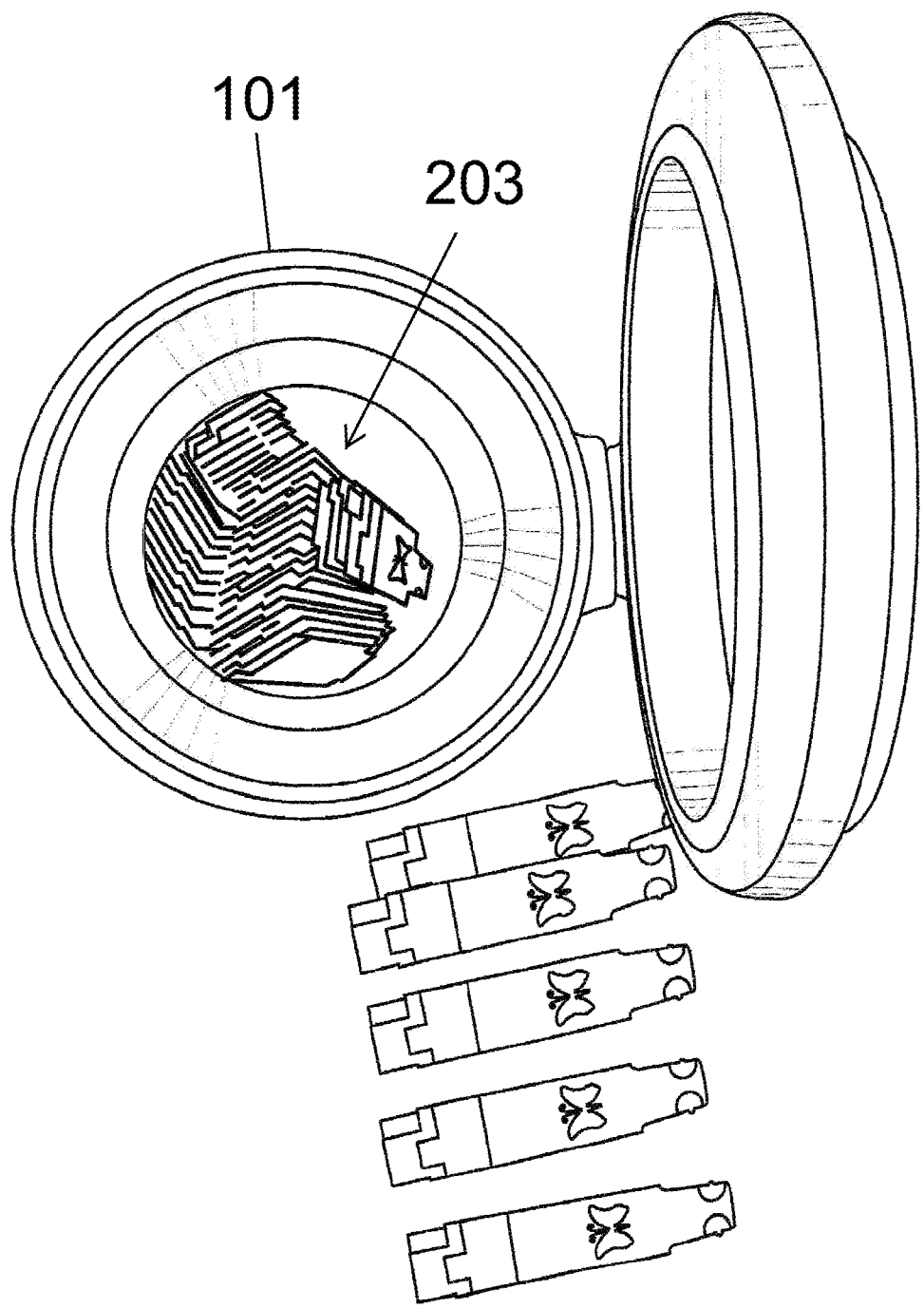
FIG. 4 is a top plan view of the container of FIG. 1 in an open position, with the diabetes test strips of FIG. 3 stacked vertically within the container.
Figure 5:
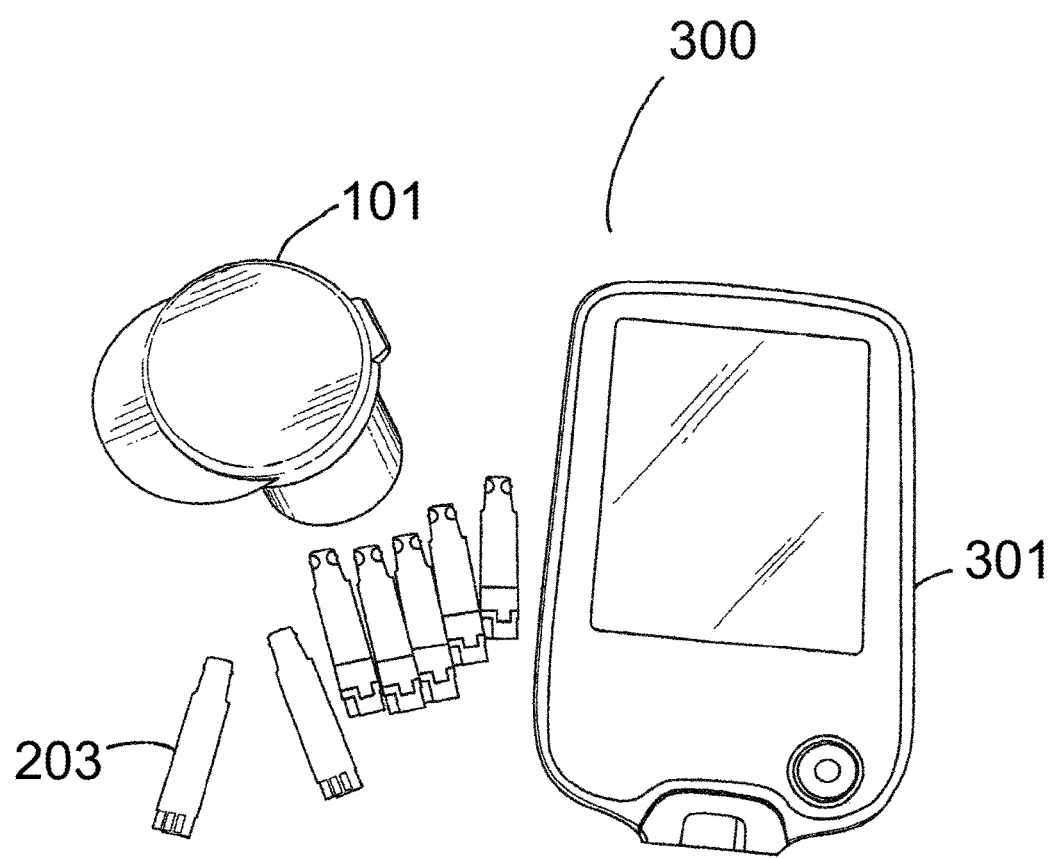
FIG. 5 is a top perspective view of a prior art container, diabetes test strips and blood glucose meter.

Conventional diabetes test strips and their containers and labeling are illustrated in FIGS. 1-5 and FIG. 18. Specifically, FIG. 1 depicts a standard test strip container 101 used in the industry, typically made from plastic or some other non-biodegradable material. As illustrated in FIG. 2, the top lid 202 of the container 101 provides a closing mechanism and snaps down onto the body of the container 101 to secure the test strips inside. Once all of the test strips are all used, the container 101 is discarded. In FIG. 3, a plurality of conventional diabetes test strips 203 are illustrated. The test strips 203 are placed into the container 101 in a vertical position relative to the height of the container 101 and are thus each positioned parallel to an adjacent test strip 203 inside of the container 101, as illustrated in FIG. 4. As depicted in FIG. 5, conventional equipment used to test blood glucose, such as a diabetes test system 300, includes a container 101 housing test strips 203 and a glucose meter 301.

As illustrated in FIG. 18, prior art labels for the front and bottom of the box used to package FreeStyle™-branded diabetes test strips manufactured by Abbott Diabetes Care Inc. of Lake Bluff, Ill. are illustrated. These labels include various codes specific to that box of diabetes test strips. For example, the illustrated NDC code 201 is issued by the Federal Drug Administration (FDA) and is required to be placed on the box before it is able to be sold in the United States marketplace. This NDC code 201 is a ten digit number that includes the manufacturer's product and package codes and is scanned at the pharmacy so that the pharmacy may be reimbursed from third-party insurance providers or Medicare and Medicaid. The box also includes other codes, such as a bar code 202 that provides other information about the product, including price information.

The invention improves upon the conventional diabetes test strip packaging to ensure the integrity of the diabetes test strips and to reduce or eliminate the presence of counterfeit products.

In one aspect of the invention, a diabetes test system is provided. The diabetes test system generally includes a kit having: (i) a glucose meter, (ii) a hand prick pen, and (iii) at least one diabetic test strip stored in a test strip container. The glucose meter, hand prick pen, and at least one diabetic test strip all function together in the diabetes test system 300 as a means for testing blood sugar levels. Each of the above-identified components is stored in the diabetes test system in its own individual compartment, to ensure protection from contamination during transporting of the test system. The diabetes test system is generally packaged into a carrying case to ensure that each of the individual components are protected. Each of these functional components is discussed in turn.

Glucose Meter

The glucose meter 301 is an electronic device for measuring blood sugar levels. Conventional glucose meters are known in the art, including glucose meters that include software for detecting the "status" of at least one diabetic test strip. The status of a diabetic test strip (hereinafter referred to as "diabetic test strip status") indicates whether the test strip is an authentic test strip safe for use by the diabetic, or whether there is some defect with the strip such that it should not be used. Once the software detects the diabetic test strip status, it may return a message to the user via the screen on the glucose meter indicating whether a blood sample should be applied to the test strip, or whether the strip is not safe to use (for example, by conveying an "ERROR" message). Alternatively, the blood glucose meter 301 can be equipped with a speaker (not shown separately) so as to announce the message or reading. This would be especially helpful for handicapped individuals.

Figure 21:
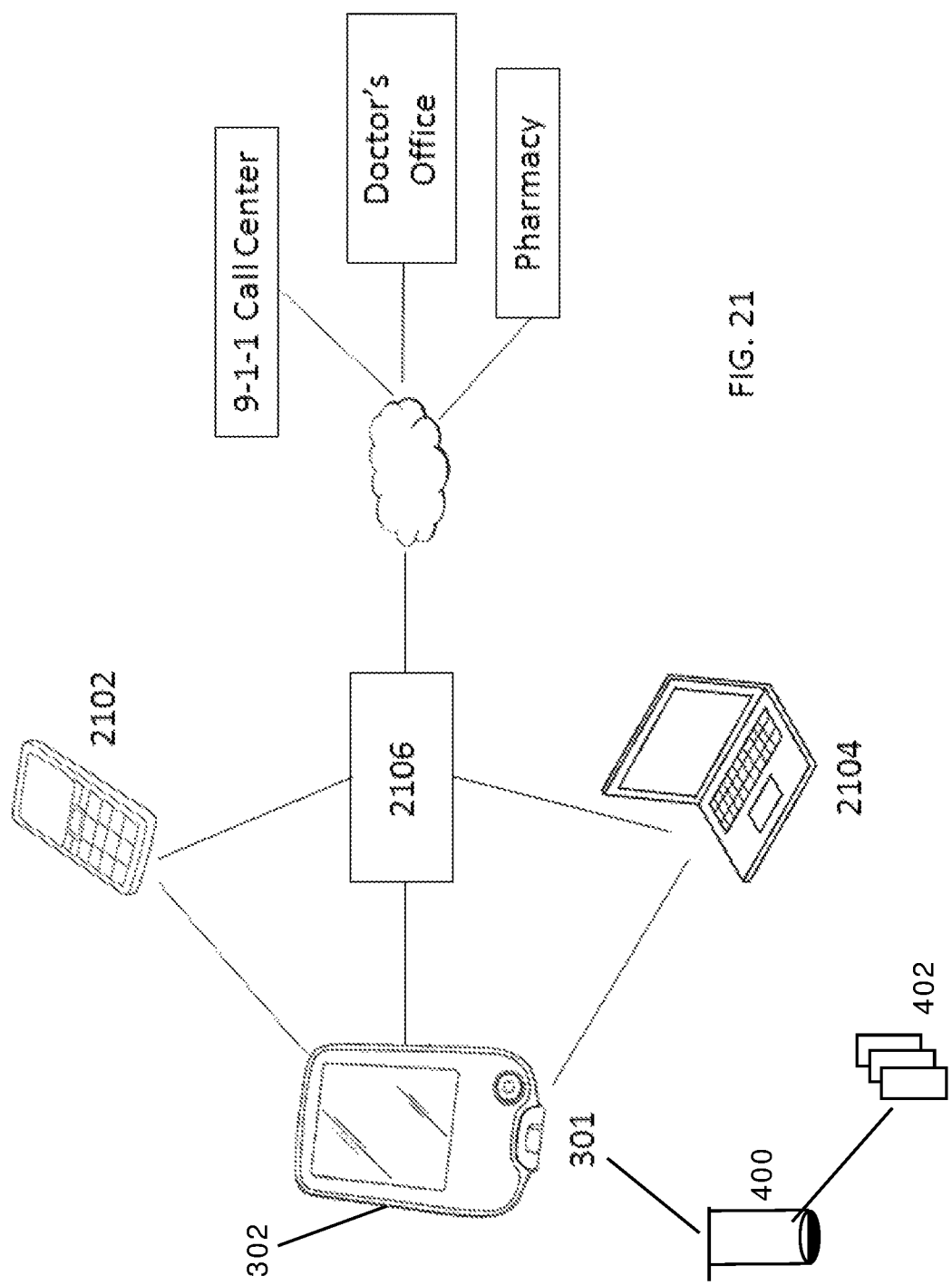
FIG. 21 is a diagram of a wireless or wired communication means for transmitting data from a blood glucose meter to other devices or servers, according to an embodiment of the invention.

In one aspect of the invention, as illustrated in FIG. 21, a glucose meter 301 is equipped internally with a communication device 302 (not shown separately) that transmits information pertaining to the authenticity of the diabetic test strip, as set forth above, or to transmit data relating to the blood glucose level of the user to a variety of sources. The communication device can be, for example, a WiFi or Bluetooth® transmission system, as are well known in the electronic arts. For example, once the glucose meter 301 measures the user's blood glucose level, that reading may be transmitted directly to the user's mobile device 2102, such as a mobile phone, or to the user's personal computer 2104. This may be done using a wired communication, such as a USB cable or Ethernet connection. Alternatively, this may also be done wirelessly, such as through WiFi by means of a router 2106, or the glucose meter 301 may be wirelessly paired to the user's mobile device 2102 or personal computer 2104 by means of Bluetooth® protocol. Further, if the glucose level of the user is dangerously high or low, the glucose meter 301 may wirelessly transmit data through the router 2106 to an outside server, such a 9-1-1 call center, to dispatch an ambulance to the user's home, or to the patient's doctor's office. In other embodiments, the communications device may wirelessly transmit data through the router 2106 to the patient's pharmacy, for purposes of renewing prescriptions or for reordering diabetes test strips when the user is running low.

Test Strip Container

Figure 6:
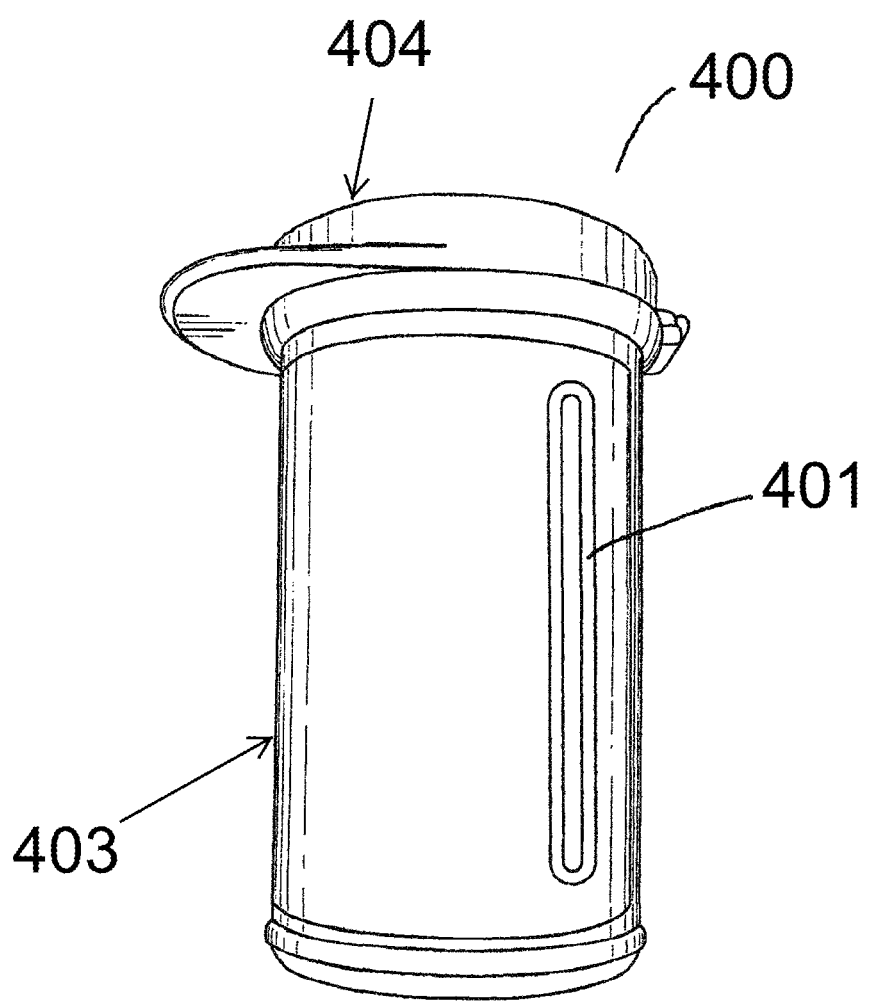
FIG. 6 is a front perspective view of a diabetic test strip container according to an embodiment of the invention.
Figure 7:
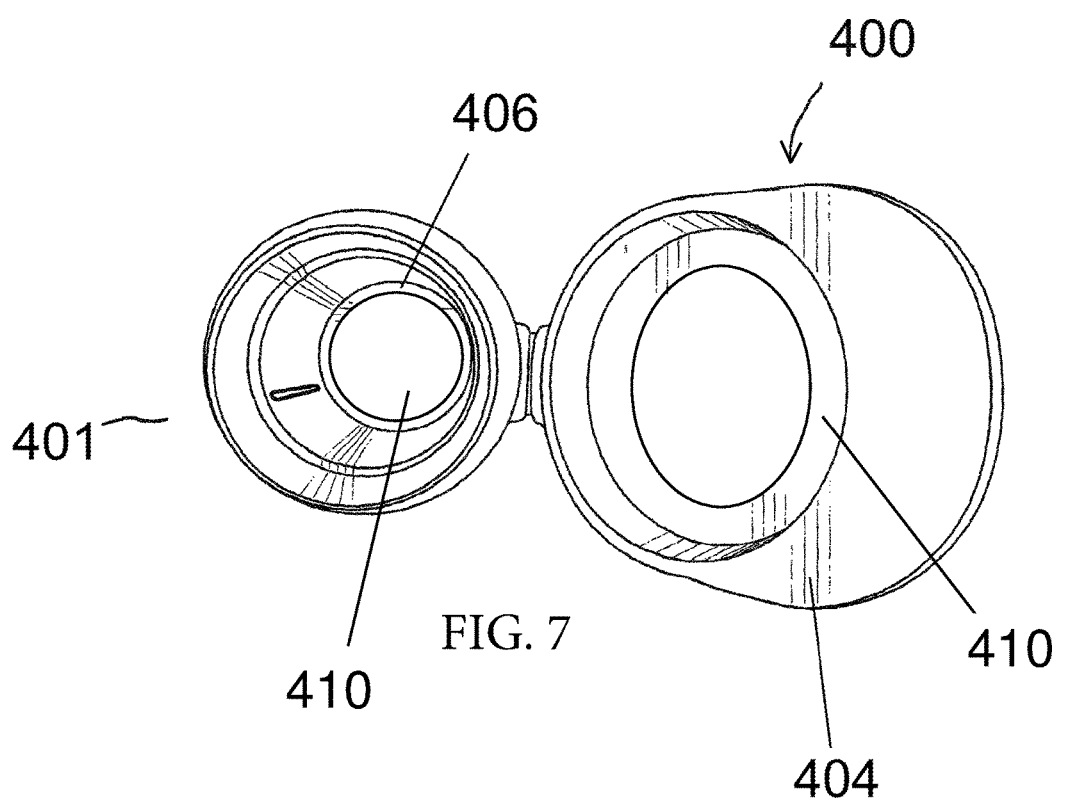
FIG. 7 is a top plan view of the container of FIG. 6 in an open position.
Figure 8:
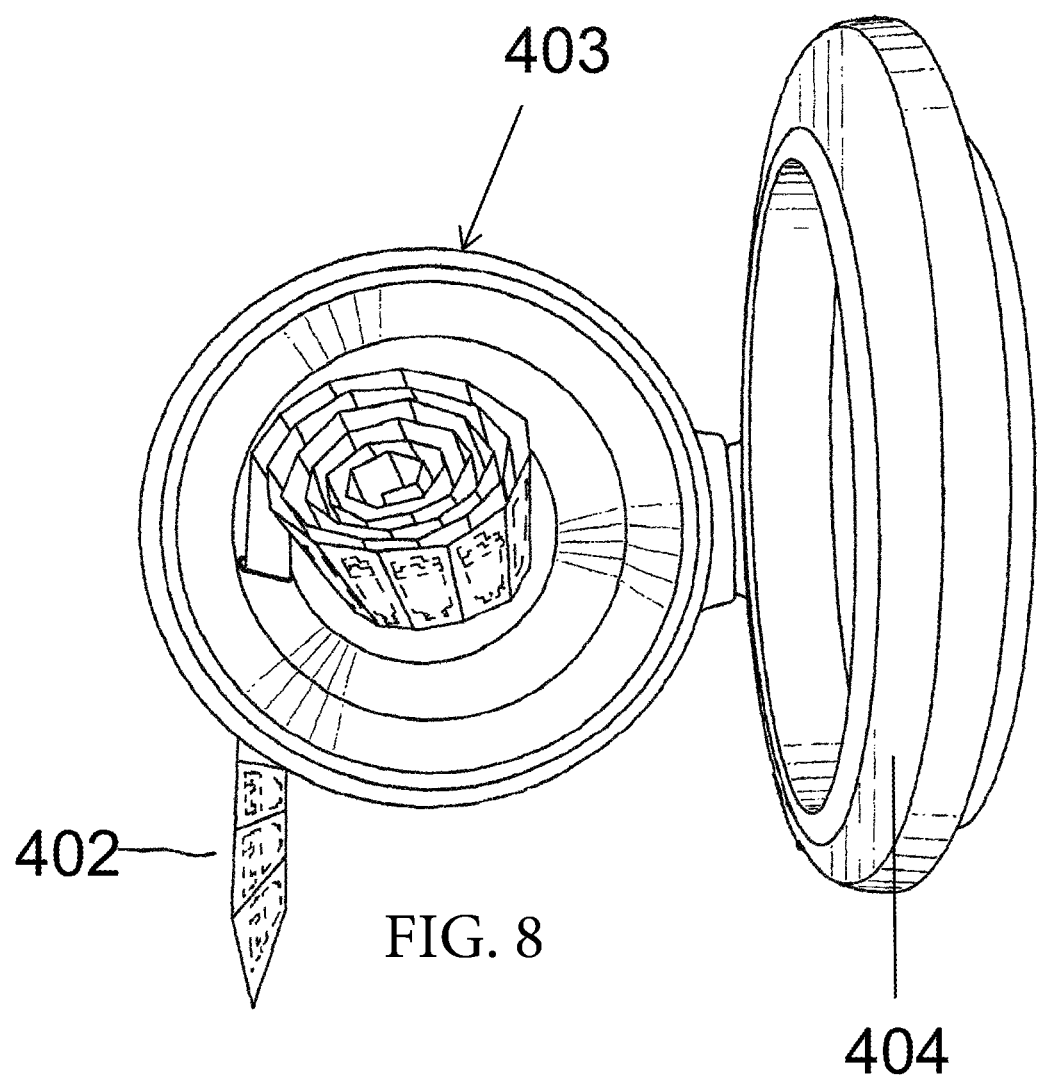
FIG. 8 is a top plan view of the container of FIG. 6 in an open position having diabetes test strips in a rolled positioned vertically within the container.

The diabetes test system also includes at least one diabetic test strip stored in some type of test strip container. In one embodiment, as shown in FIGS. 6-8, a test strip container 400 is provided which is used to store at least one diabetic test strip. The test strip container 400 is generally formed as a cylindrical, unitary body 403 ("the container body") having a container lid 404. The container body 403 preferably has a dispensing slot 401, which includes a slot seal (not shown). The dispensing slot 401 allows an individual diabetic test strip, which is stored vertically within the container 400, to be dispensed from the container for use by a diabetic. The slot seal ensures that contaminants are unable to enter the container body 403, thus minimizing or eliminating contamination of the diabetes test strips stored within. The container lid 404, which is hinged to the top of the container body 403, snaps down over an opening 406 at the top of the container body 403 to protect the at least one diabetic test strip or roll of sealed diabetes test strips 402 stored inside from contamination, as illustrated in FIGS. 7 and 8. As shown in FIG. 8, when a roll of sealed diabetes test strips 402 is placed inside of the container 400, the end of the roll is fed through the dispensing slot 401 such that the user can easily detach an individual diabetic test strip 203 from the roll 402.

In one embodiment, the container body 403 may include vibration damping materials 410 to reduce the vibrational forces imposed on the test strips stored within. In one embodiment, the inside of the container body 403 is lined with vibration damping materials, such as cotton, bubble wrap, or a combination of both. In another embodiment, the container body 403 may include a label which contains written indicia to convey information to the user relating to the diabetes test strips stored within.

Diabetes Test Strips

Figure 9:
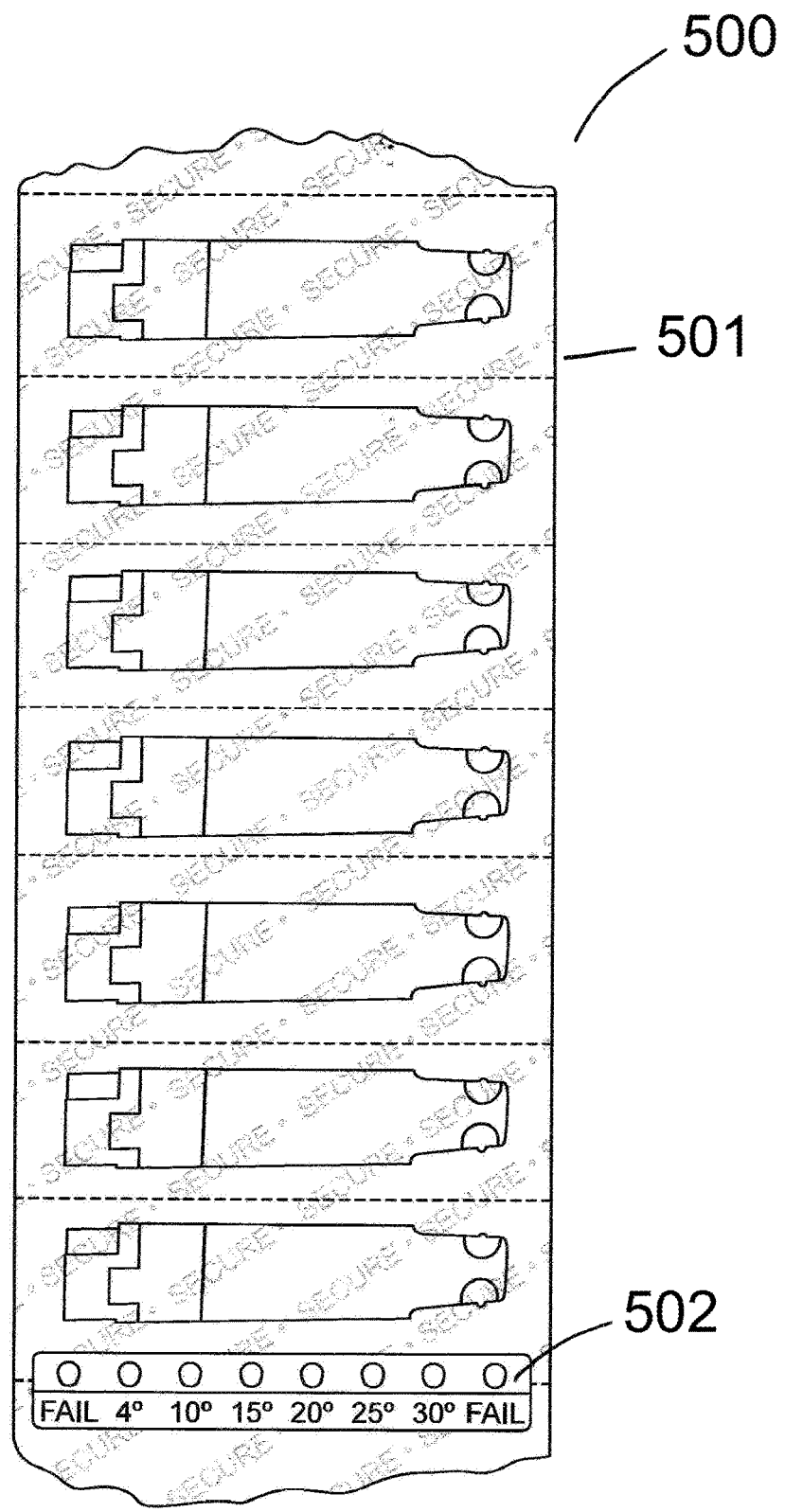
FIG. 9 is a top plan view of a flat strip of sealed diabetes test strips having anti-counterfeiting packaging and historical temperature tagging in accordance with an embodiment of the invention.
Figure 10:
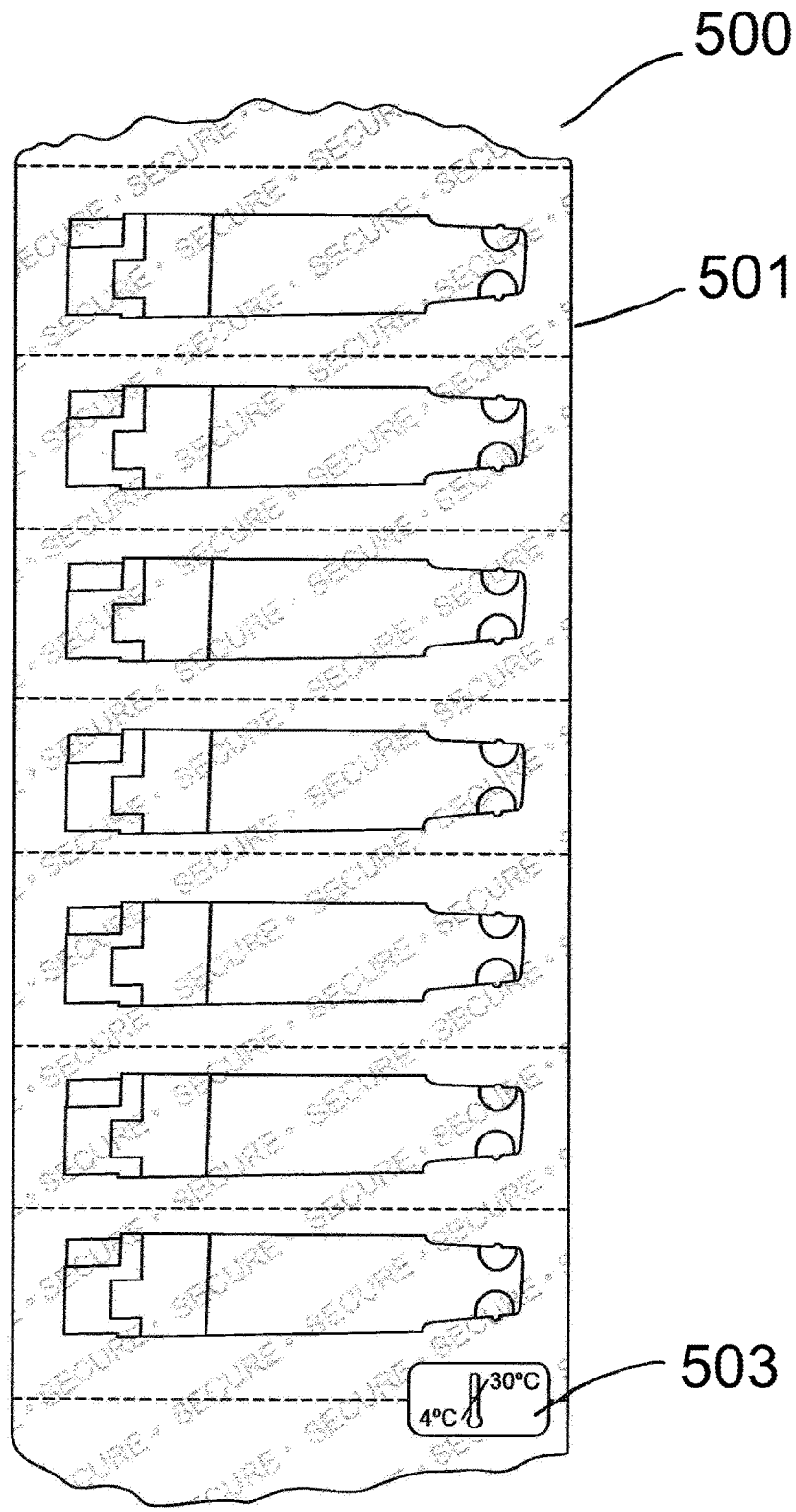
FIG. 10 is a top plan view of a flat strip of sealed diabetes test strips having anti-counterfeiting packaging and alternate pass/fail temperature tagging in accordance with an embodiment of the invention.
Figure 11:
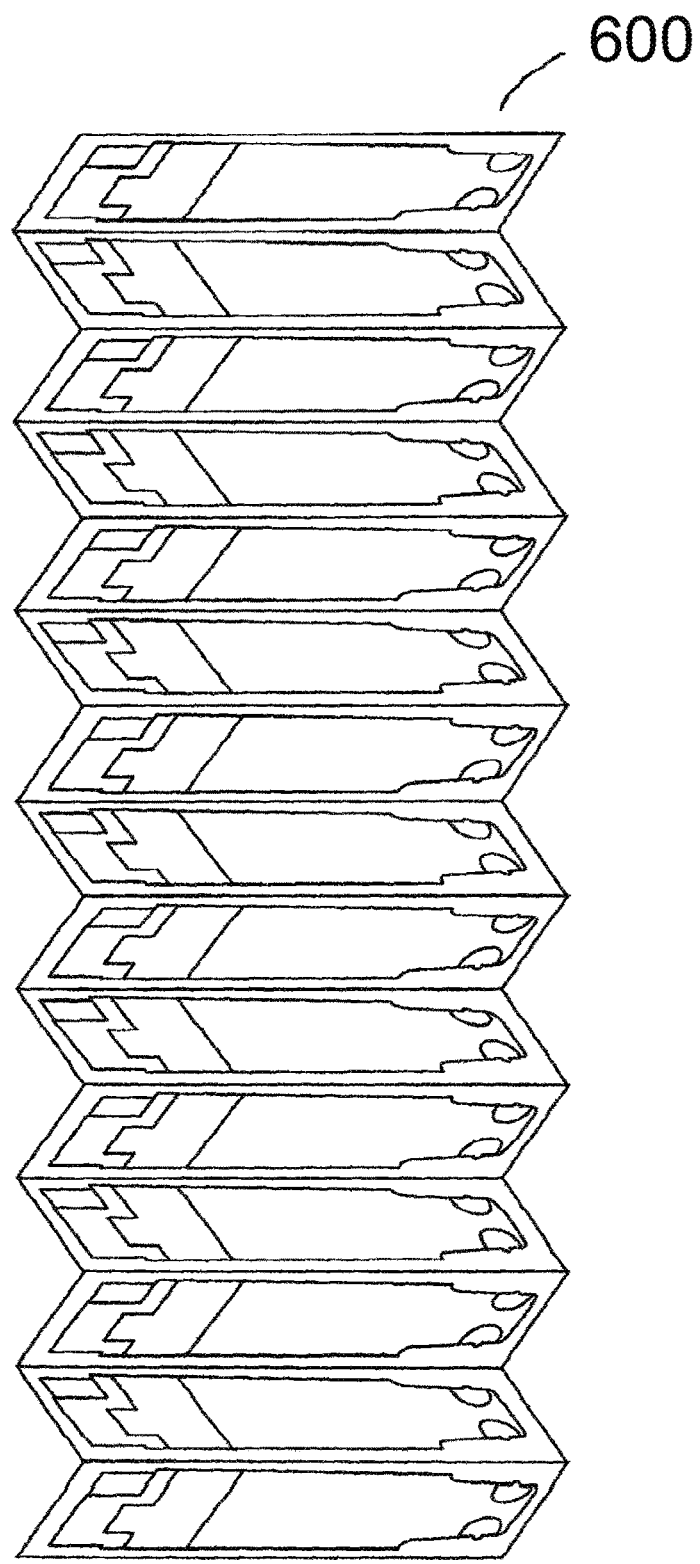
FIG. 11 is a top plan view of a folded strip of individual diabetes test strips in accordance with an embodiment of the invention.

Exemplary strips of diabetes test strips are shown in FIGS. 9-11. Each diabetic test strip may be formed from plastic or any other suitable material or combination of materials. In FIG. 9, a strip 500 of a plurality of securely packaged 501 diabetes test strips 203 with a graduated temperature indicator 502 are illustrated. The graduated temperature indicator 502 is a temperature sensor that visually records temperatures to which the test strip package 501 has been exposed, so that the user may be alerted not to use a diabetic test strip 203 that has been exposed to extreme high or low temperatures. For example, the graduated temperature indicator 502 includes a marking area for a range of temperatures in increments of about 5° C., such as 4°, 10°, 15°, 20°, 25°, and 30°, all of which are still within the safe range of temperatures. Anything below the lower limit and above the upper limit is marked with a "FAIL" indicator, such that, if the marking areas above or below the FAIL indicator is filled in, the user knows that that particular strip 500 has been exposed to temperatures above or below the safe temperature range.

In an alternative embodiment illustrated in FIG. 10, the strip 500 of the plurality of packages 501 of diabetes test strips 203 includes a graduated temperature indicator 503 that works as a PASS/FAIL temperature indicator. In this embodiment, the PASS/FAIL temperature indicator 503 simply provides a marking area for the lower and upper limits (4° C. and 30° C., respectively) of the safe range of temperatures, such that it can alert the user as to whether that particular strip 500 of a plurality of securely packaged 501 diabetes test strips 203 has been exposed to temperatures within the "FAIL" range.

In another embodiment, a graduated temperature indicator may be placed on the test strip container 400 itself (not shown), in place of or in addition to a graduated temperature indicator 502 or 503 being placed on the strip 500 of a plurality of securely packaged 501 diabetes test strips 203.

In yet another embodiment (not shown), the strip 500 of a plurality of securely packaged 501 diabetes test strips 203 or the test strip container 400 may include a vibration indicator that functions similarly to the graduated temperature indicators 502 or 503. Specifically, the vibration indicator includes a sensor that records vibrational forces to which the strip 500 or container 400 has been exposed, so that the user may be alerted not to use a diabetic test strip that has been exposed to high vibrational forces. Examples of suitable vibration indicators include, but are not limited to, active vibration sensor RFID tags, such as those manufactured by GAO RFID Inc. of Toronto, Ontario, Canada or LORD MicroStrain of Williston, Vt.

In FIG. 11, another embodiment of a strip 600 of a plurality of diabetes test strips is illustrated. In this embodiment, each of the diabetes test strips is foldable relative to the next test strip, such that the entire strip 600 may be folded in an accordion style. This allows for ease of packaging of the diabetes test strips in their shipping box or when placed within the test strip container, such as test strip container 400. Each individual diabetic test strip package may be separated from its adjacent test strips by means of perforation in the packaging, to allow the user to easily detach one individual test strip package from the next. Each of these packages may be a secure package as discussed elsewhere herein.

Figure 12:
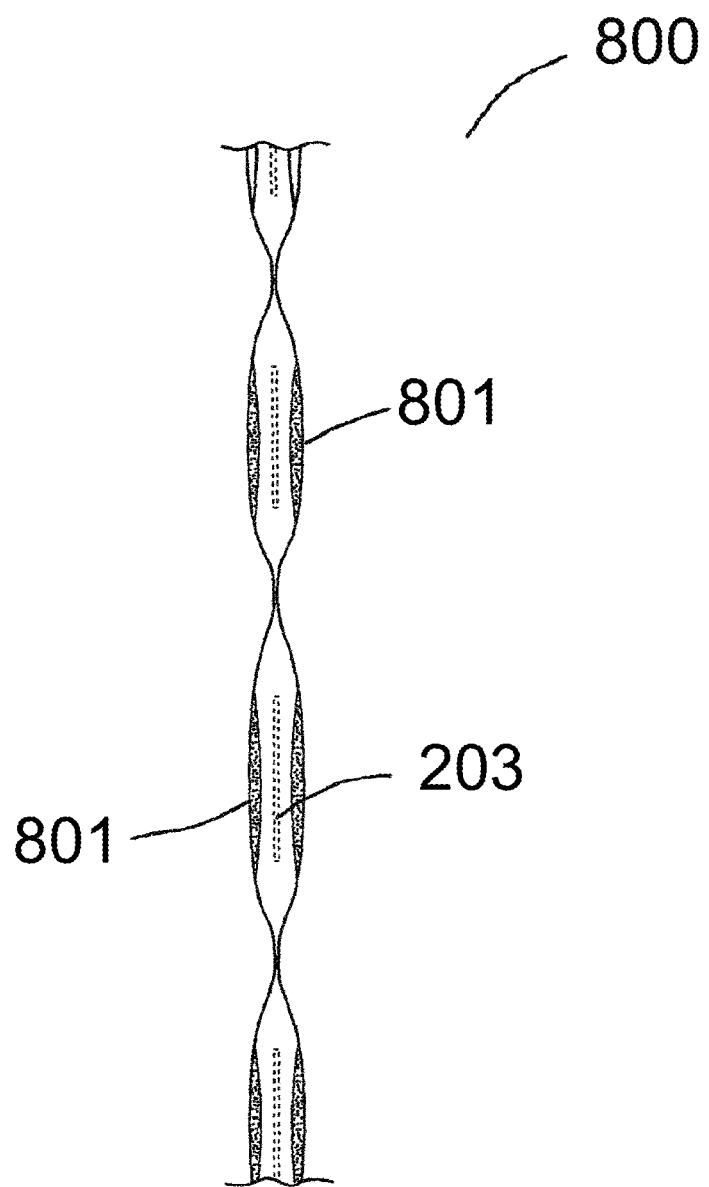
FIG. 12 is a side cross-sectional view of the strip of diabetes test strips illustrated in FIGS. 9 and 10 having a vibration absorbing lining in accordance with an embodiment of the invention.

To reduce the effect of vibrational forces to which the diabetes test strips are subjected, vibration damping materials may be included within a strip 800 of a plurality of diabetes test strips 203, such as that illustrated in the cross-sectional view of FIG. 12. Here, there is a vibration absorbent material 801 applied to the top surface of the strip 800 and a vibration absorbent material 801 applied to the bottom surface of the strip 800. In this way, each individual diabetes test strip 203 is surrounded by vibration damping materials.

Figure 13:
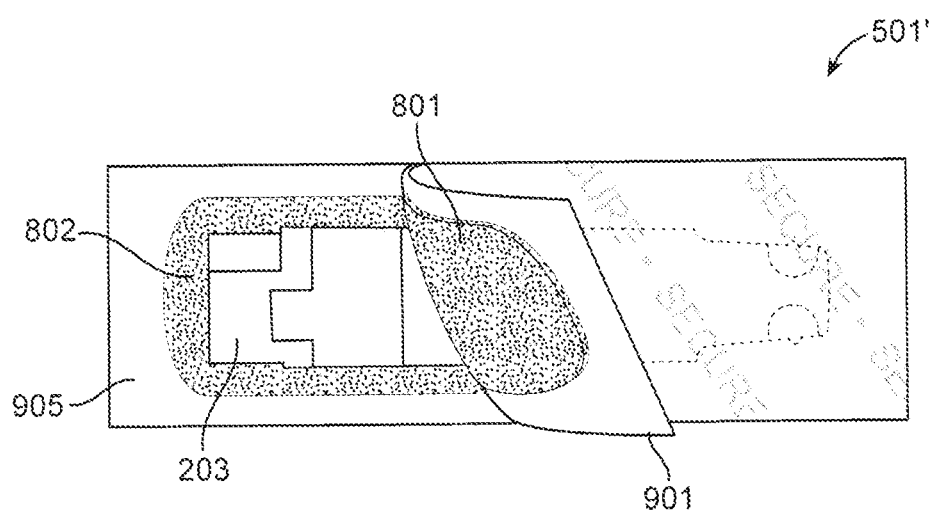
FIG. 13 is a top plan view of a test strip with anti-counterfeiting packaging and an anti-vibration lining on the top and bottom of the packaging in accordance with an embodiment of the invention.

Similarly, in FIG. 13, an individual diabetes test strip package 501' is illustrated with its top layer 901 pulled back, showing a vibration absorbent material 801 bonded to the top layer 901 of the secure package 501'. A vibration absorbent material 801 is also applied to the bottom layer 905 of the test strip package 501'. The test strip 203 is inserted between the top layer 901 and the bottom layer 905 of the test strip package 501' and is thus surrounded by the vibration damping materials 801. Each of the secure test strip packages 501' can be the same as each of the perforated secure test strip packages 501, except they are meant to be individually dispensed, whereas the secure test strip packages 501 are meant to be dispensed as part of a strip 500 of a plurality of securely packaged 501 diabetes test strips 203.

Figure 14:
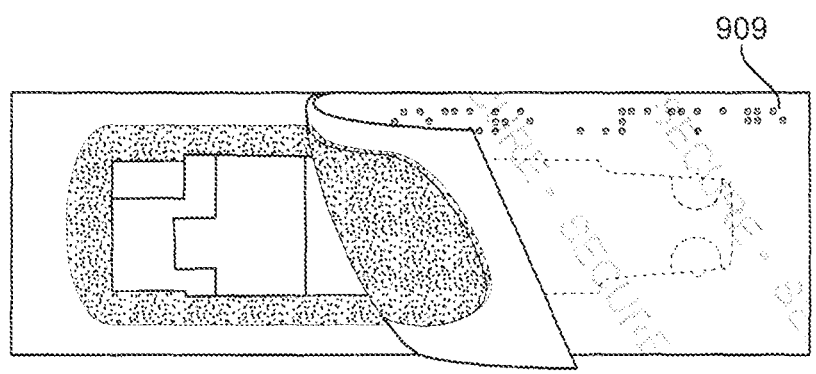
FIG. 14 is a top plan view of a diabetic test strip having Braille instructions placed on a sealed anti-counterfeiting diabetic test strip in accordance with an embodiment of the invention.

In another embodiment, FIG. 14 illustrates an individually packaged diabetes test strip package 501' having Braille instructions 909 imprinted on a surface of the strip package 501'. The Braille instructions 909 provide for ease of use by blind persons. In another embodiment (not shown), the test strip container 400 and/or the label on the box of diabetes strip strips may include Braille for blind users.

Figure 15:
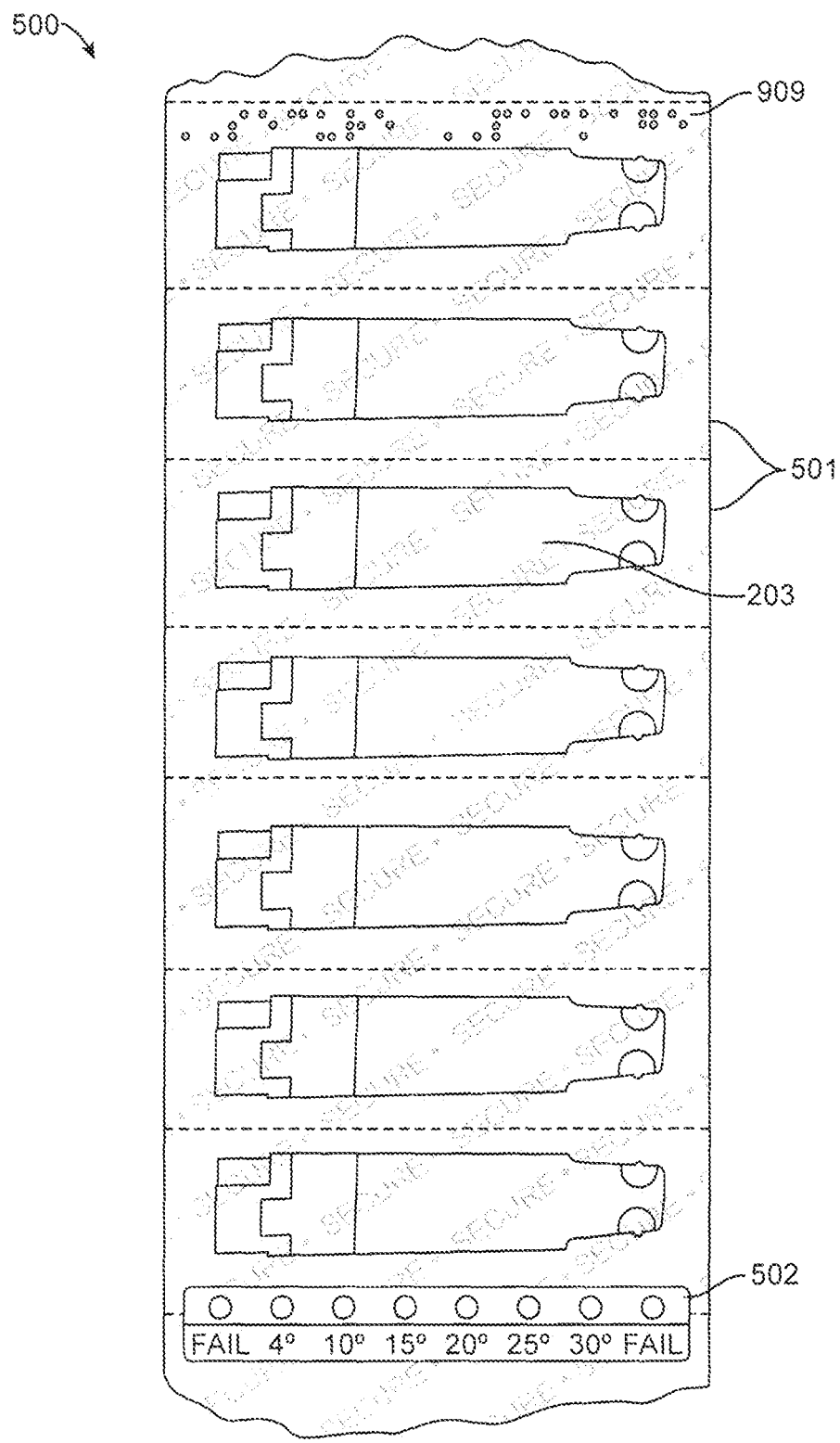
FIG. 15 is a top plan view of a diabetic test strip having Braille instructions placed on a flat strip of sealed diabetes test strips with anti-counterfeiting packaging and historical temperature record in accordance with an embodiment of the invention.
Figure 16:
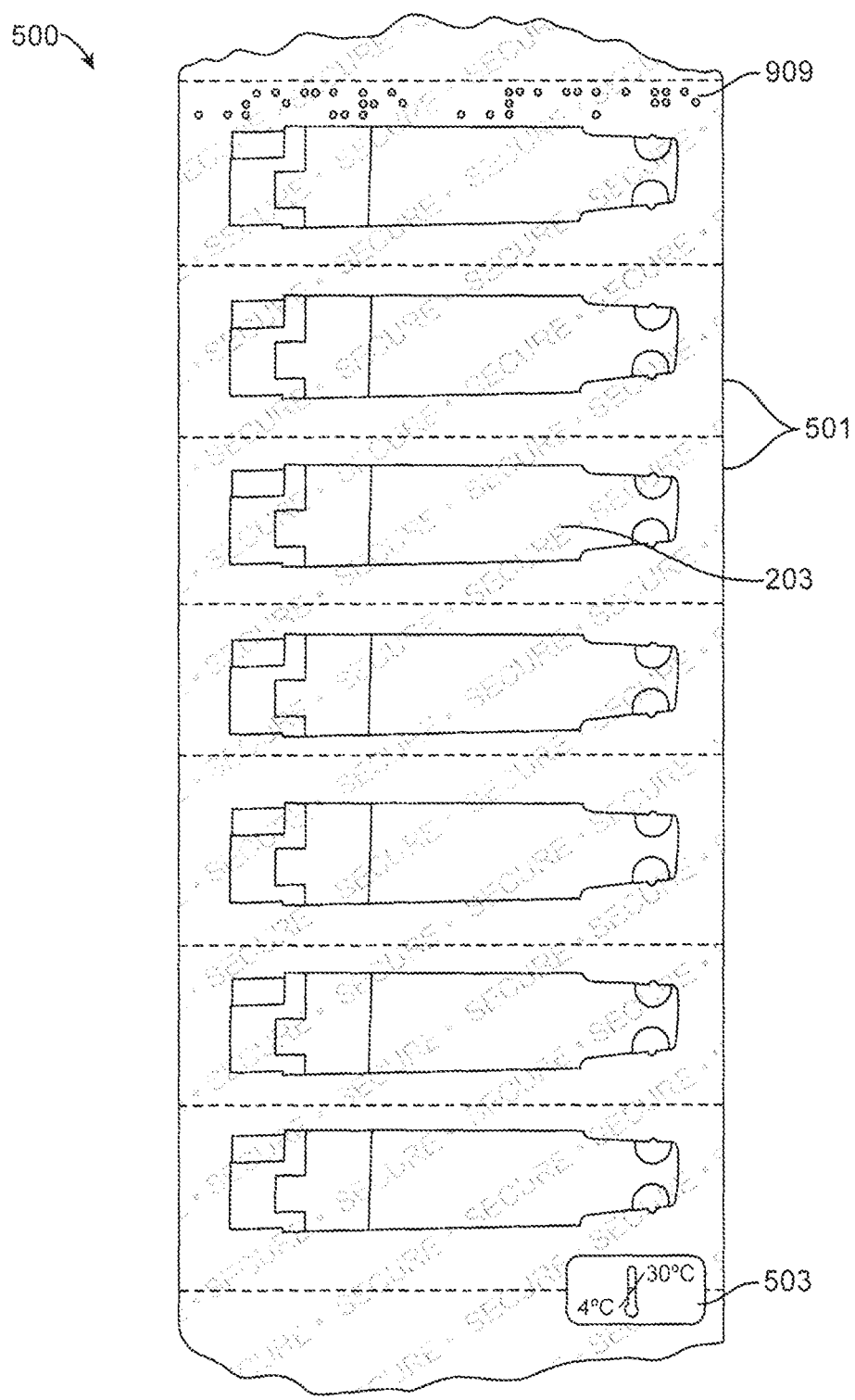
FIG. 16 is a top plan view of a diabetic test strip having Braille instructions placed on a flat strip of sealed diabetes test strips with anti-counterfeiting packaging and pass/fail temperature tagging in accordance with an embodiment of the invention.

FIG. 15 illustrates a strip 500 of a plurality of secure diabetes test strip packages 501 having Braille instructions 909 imprinted on a surface of the strip 500. In this embodiment, the strip 500 also includes a graduated temperature indicator 502. Alternatively, FIG. 16 illustrates a strip 500 of a plurality of secure diabetes test strip packages 501 having Braille instructions 909 imprinted on a surface of the strip 5000, the same as shown in FIG. 15, but this strip 500 includes a PASS/FAIL temperature indicator 503, such as the PASS/FAIL temperature indicator 503 illustrated in FIG. 10.

The diabetes test strips of the invention may further include a secure marker indicator. The secure marker indicator provides a mechanism for identifying relevant manufacturing data and historical data relating to the diabetes test strips to the user, including the country of origin of the test strips. Such information would be maintained on remote servers. The secure marker indicator may include programmable and updatable intelligence capability. For example, the secure marker indicator may be an RFID tag that is placed on a strip of diabetes test strips, on the test strip container body, or on the outside of a box of diabetes test strips, in order to track the container of the diabetes test strips to reduce the occurrence of gray market sales and counterfeiting. Alternatively, any other indicia that may be read electronically and then transmitted over the Internet, could be used. Furthermore, a GPS or other satellite tracking system could also be implemented, with appropriate sensors placed on the diabetes test strip packages or the containers containing those diabetes test strips. Such systems are in common use for tracking, for example, the locations of long distance trucks. In that manner, the location of the packages of diabetes test strips or containers containing those diabetes test strips can be tracked.

Figure 17:
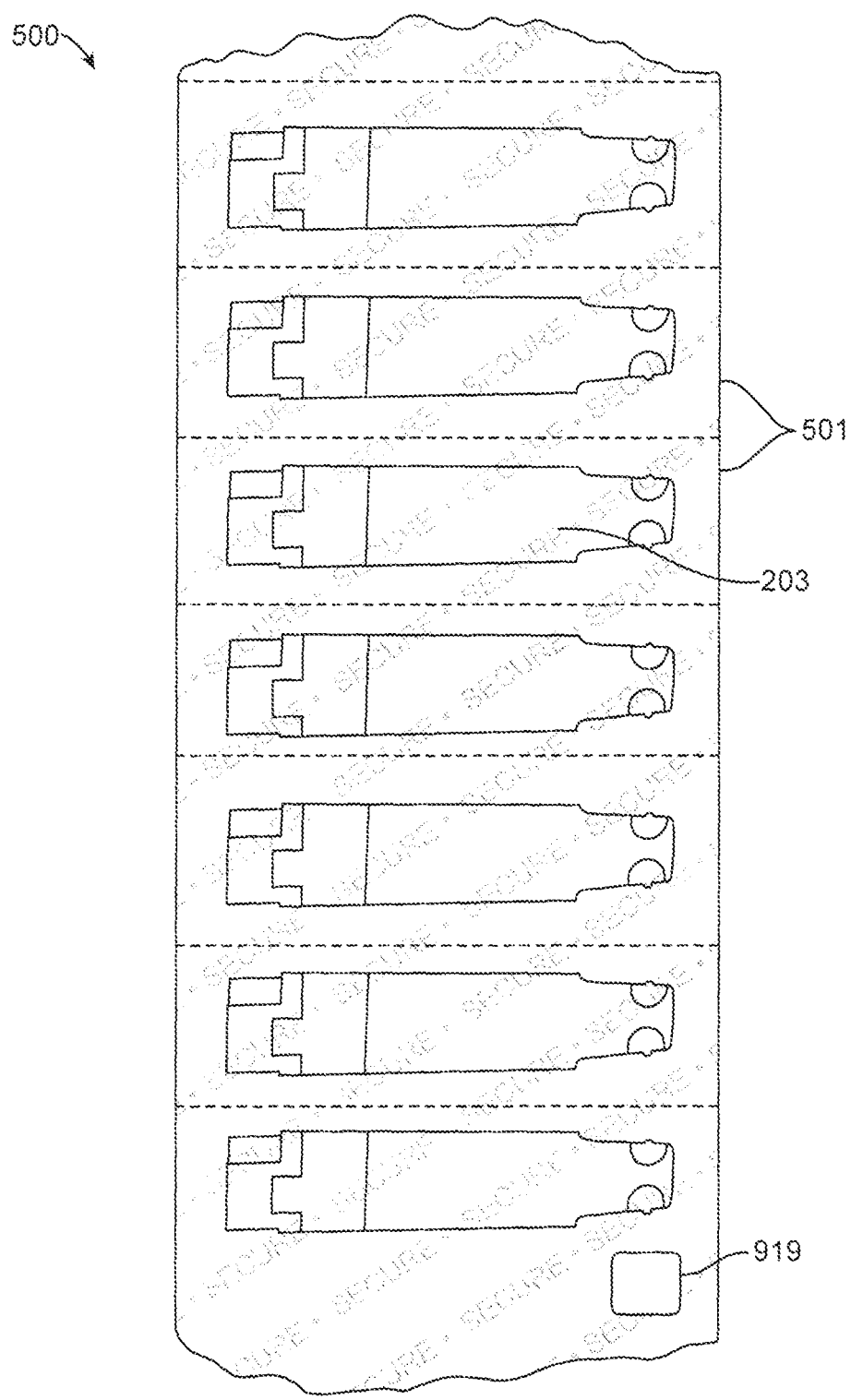
FIG. 17 is a top plan view of a strip of sealed diabetes test strips with anti-counterfeiting packaging having an RFID tag on the strip in accordance with an embodiment of the invention.

In one embodiment, as illustrated in FIG. 17, an RFID tag 919 may be placed on a surface of a strip 500 of a plurality of secure diabetes test strip packages 501 of test strips 203 to provide a "one-time" verification means. In use, once the diabetes test strips arrive at a pharmacy, the pharmacy would scan the RFID tag 919 as they would the NDC code 201 illustrated in FIG. 18. The RFID tag 919 functions as a one-time verification means because each time the RFID tag 919 is scanned, that scan is sent to and recorded in a central database, such as the manufacturer's database or a database of the U.S. government. When the RFID tag 919 is scanned by the pharmacy, the pharmacy's computer system would communicate with that central database to determine whether that particular RFID tag 919 has even been scanned. If it has, the database would transmit such data to the pharmacy's computer system, which would alert the pharmacy that this particular item is a gray market good.

FIG. 19 shows labeling for the FreeStyle Lite®-branded test strips, manufactured by Abbott Diabetes Care Inc., with the addition of an RFID tag 919 on the bottom of the box to achieve the same function as RFID tag 919 as illustrated in FIG. 17. In this embodiment, the RFID tag 919 is simply placed on the outside of the box of diabetes test strips for ease of scanning by the pharmacy. Likewise, FIG. 20 illustrates another label for the FreeStyle Lite®-branded test strips with the addition of an RFID tag 919 on the front of the box, also for ease of scanning by the pharmacy.

In another embodiment, hologram markings (not shown) may be included on a strip 500 of a plurality of diabetes test strip packages 501, on a test strip container body, or on the outside of a box of diabetes test strips to track gray market goods and monitor shipments.

Method of Use of the Diabetes Test System

Figure 22:
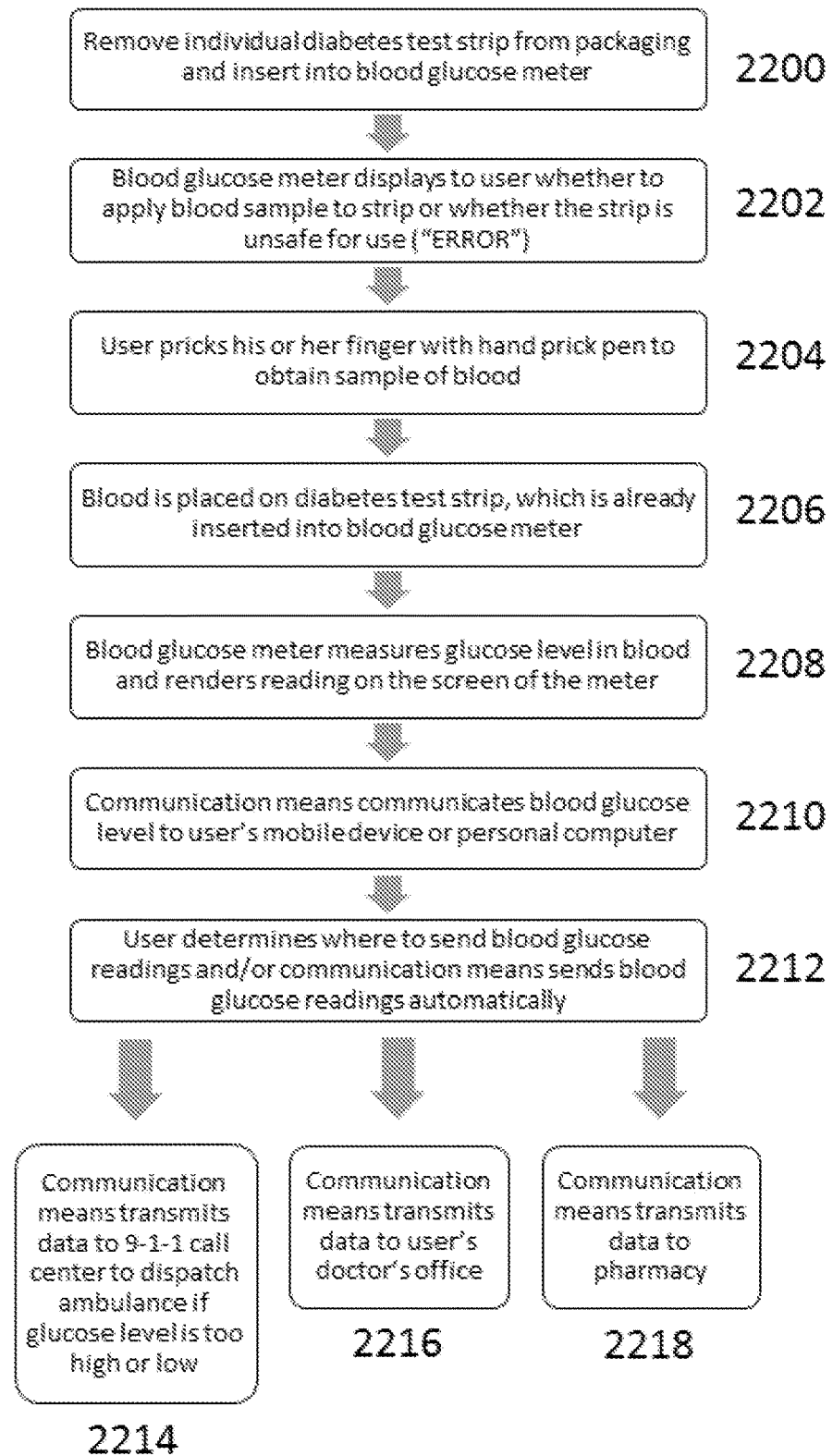
FIG. 22 is a flowchart of a method of using a diabetes test system according to an embodiment of the invention.

As illustrated in FIG. 22, the user would remove an individual diabetes test strip from its packaging and insert it into the blood glucose meter, as set forth in Step 2200. The blood glucose meter then determines whether the test strip is safe for use and displays to the user either: (1) instructions to apply a blood sample to the strip, or (2) an "ERROR" message indicating that it is unsafe for use, as set forth in Step 2202. Next, the user would prick his or her finger with a hand prick pen, to obtain a sample of blood, as set forth in Step 2204. The blood is then placed on the diabetes test strip, which is already inserted into the blood glucose meter 301, as indicated in Step 2206. The blood glucose meter then measures the glucose level in the user's blood and renders a reading on the screen of the meter, as shown in Step 2208. In one embodiment illustrated in Step 2210, the communication device of the blood glucose meter 301 then communicates the user's blood glucose level to the user's mobile device 2102 or personal computer 2104, as shown in FIG. 21. The user's mobile device 2102 or personal computer 2104 may be running an app or software that receives the information from the blood glucose meter 301, and then saves and processes the received data for further use, if desired.

In a further embodiment illustrated in Step 2212, the user then determines where to send the blood glucose readings, if anywhere, or the readings are automatically sent to an external device without waiting for user inputs. For example, in the event that the user's blood glucose level is dangerously high or low, the communication device of the glucose meter, the user's mobile device and/or the user's personal computer may transmit data to a 9-1-1 call center to dispatch an ambulance, as set forth in Step 2214. In yet another embodiment shown in Step 2216, the communication device, the user's mobile device 2302 and/or personal computer 2304 may also transmit data to the patient's doctor's office for purposes of notifying the doctor of the patient's reading, or for the purpose of renewing the patient's prescriptions. In Step 2218, the communication device, the user's mobile device 2302 and/or personal computer 2304 may further transmit prescription information to a pharmacy or place an order for diabetes test strips if the user is running low. Steps 2214 through 2218 may each be done individually or may done simultaneously depending on the blood glucose reading and inputs from the user. It is contemplated that the instant invention could include a blood glucose meter assembly (not shown), that provides the sensor portion of an existing blood glucose meter and that is electrically coupled, either by wire or wirelessly, with the user's mobile device for performing the computing and transmitting portions of the blood glucose meter described above, using an app running on the mobile device.

Although this invention has been described in connection with specific forms and embodiments thereof, it will be appreciated that various modifications other than those discussed above may be resorted to without departing from the spirit or scope. For example, equivalent elements may be substituted for those specifically shown and described, certain features may be used independently of other features, and in certain cases, particular locations of elements may be reversed or interposed, all without departing from the spirit or scope as defined in the appended Claims.

What is claimed:

1. A diabetes test combination for measuring the blood glucose level of a user, the combination comprising:
    at least one external device comprising a remote computer server, a mobile phone, a personal computer, a router, or a combination thereof;
    a glucose meter comprising a wired or wireless communication device able to transmit data related to a user's blood glucose level to at the least one external device, wherein said wireless communication device comprises a WiFi communication device, a Bluetooth communication device, or a combination thereof, and is housed within the glucose meter, and wherein the wired communication device comprises a USB communication device, an Ethernet communication device, or a combination thereof;
    at least one diabetic test strip;
    a container for storing the at least one diabetic test strip, the container formed of a cylindrical body having a vertical dispensing slot formed therein, the dispensing slot enclosed by a slot seal;
    wherein the at least one diabetic test strip or the container further comprises a vibrational damping material comprising cotton, bubble wrap, or a combination thereof that is applied to a top surface and a bottom surface of the diabetic test strip, or applied to line the inside of the container; and
    wherein the at least one diabetic test strip, or the container, further comprises a vibration indicator comprising vibration sensor RFID tags, which visually identifies to the user the vibration forces to which the at least one diabetic test strip or the container has been exposed.

2. The diabetes test combination of claim 1, wherein said wireless communication device is the WiFi communication device.

3. The diabetes test combination of claim 1, wherein said wired communication device is the USB communication device.

4. The diabetes test combination of claim 1, wherein the diabetes test combination further comprises:
   a box comprising at least one diabetic test strip;
   a graduated temperature indicator, comprising a temperature sensor that is able to display temperatures that the test strip has been exposed to: as a range of increments of safe temperatures and as failed if not within the range, or as a pass fail indicator,
   a secure marker indicator, comprising a sensor able to track and/or locate at least one test strip and/or the container, or a combination thereof; and,
      wherein said indicators are located on at least one diabetes test strip, and/or on the container, and/or on the box comprising the at least one diabetes test strip.

5. The diabetes test combination of claim 4, wherein the secure marker indicator comprises an RFID tag, and/or a global positioning system sensor, which is able to be scanned to determine the authenticity of the diabetes test strip based on a manufacturer data, a country of origin, and/or tracking of previous locations of the containers.

6. The diabetes test combination of claim 1, wherein the at least one diabetic strip or the container further includes Braille to convey instructions about the diabetes test to a handicapped user.

7. The diabetes test combination of claim 1, wherein a plurality of at least one diabetes test strips are packaged together as an elongated strip, wherein an individual test strip is separable at the container slot.

8. The diabetes test combination of claim 7, wherein at least one of a graduated temperature indictor, a vibration indicator, a secure marker indicator, and Braille instructions, are positioned on an outer surface of the elongated strip.

9. The diabetes test combination of claim 1, wherein the glucose meter's communication device is able to transmit data to the mobile device and the personal computer, directly or through the router, and the router is able to transmit the data wirelessly to the remote computer server.

10. The diabetes test combination of claim 4, wherein the box, container, or strip is affixed with a hologram.

* * * * *